US00PP30236P2

(12) United States Plant Patent
Wood

(10) Patent No.: US PP30,236 P2
(45) Date of Patent: Feb. 26, 2019

(54) ***BUDDLEIA* PLANT NAMED 'SMNBDL'**

(50) Latin Name: *Buddleia davidii*
Varietal Denomination: SMNBDL

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/732,298

(22) Filed: Oct. 20, 2017

(51) Int. Cl.
*A01H 5/02* (2018.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Buddleia* plant named 'SMNBDL', characterized by its compact, upright and outwardly spreading plant habit; freely branching habit, thick stems with short internodes; dense and bushy appearance; broad, leathery and durable leaves; freely flowering habit; large and dense conical inflorescences with numerous violet-colored flowers; and good garden performance.

2 Drawing Sheets

Botanical designation: *Buddleia davidii.*
Cultivar denomination: 'SMNBDL'.

BACKGROUND OF THE INVENTION

The present invention relates to a new and distinct *Buddleia* plant, botanically known as *Buddleia davidii* and hereinafter referred to by the name 'SMNBDL'.

The new *Buddleia* plant is a product of a planned breeding program conducted by the Inventor in Grand Haven, Mich. The objective of the breeding program was to create new compact *Buddleia* plants with strong branches and attractive flower coloration.

The new *Buddleia* plant originated from a cross-pollination conducted by the Inventor in 2012 in Grand Haven, Mich. of a proprietary selection of *Buddleia davidii* identified as code designation UC 701, not patented, as the female, or seed, parent with *Buddleia davidii* 'Pink Delight', not patented, as the male, or pollen, parent. The new *Buddleia* plant was discovered and selected by the Inventor as a single flowering plant within the progeny of the stated cross-pollination in a controlled environment in Grand Haven, Mich. in 2014.

Asexual reproduction of the new *Buddleia* plant by softwood stem cuttings in a controlled environment in Grand Haven, Mich. since 2014 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNBDL'. These characteristics in combination distinguish 'SMNBDL' as a new and distinct *Buddleia* plant:

1. Compact, upright and outwardly spreading plant habit.
2. Freely branching habit, thick stems with short internodes; dense and bushy appearance.
3. Broad, leathery and durable leaves.
4. Freely flowering habit.
5. Large and dense conical inflorescences with numerous violet-colored flowers.
6. Good garden performance.

Plants of the new *Buddleia* differ primarily from plants of the female parent selection in flower color as plants of the female parent selection have pink-colored flowers.

Plants of the new *Buddleia* differ primarily from plants of the male parent, 'Pink Delight', in the following characteristics:

1. Plants of the new *Buddleia* are more compact than plants of 'Pink Delight'.
2. Plants of the new *Buddleia* and 'Pink Delight' differ in flower color as plants of 'Pink Delight' have pink-colored flowers.

Plants of the new *Buddleia* can also be compared to plants of *Buddleia weyeriana* X *Buddleia davidii* 'Pink Pagoda', disclosed in U.S. Plant Pat. No. 23,214. In side-by-side comparisons, plants of the new *Buddleia* differ primarily from plants of 'Pink Pagoda' in the following characteristics:

1. Plants of the new *Buddleia* are more compact than plants of 'Pink Pagoda'.
2. Inflorescences of plants of the new *Buddleia* are larger and denser than inflorescences of plants of 'Pink Pagoda'.
3. Plants of the new *Buddleia* and 'Pink Pagoda' differ in flower color as flowers of plants of 'Pink Pagoda' are pink in color.

BRIEF DESCRIPTION OF THE PHOTOGRAPHS

The accompanying colored photographs illustrate the overall appearance of the new *Buddleia* plant showing the colors as true as it is reasonably possible to obtain in colored reproductions of this type. Colors in the photographs may differ slightly from the color values cited in the detailed botanical description which accurately describe the colors of the new *Buddleia* plant.

The photograph on the first sheet is a side perspective view of a typical flowering plant of 'SMNBDL' grown in an outdoor nursery.

The photograph on the second sheet is a close-up view of a typical inflorescence of a plant of 'SMNBDL' grown in an outdoor nursery.

DETAILED BOTANICAL DESCRIPTION

The aforementioned photographs and following observations, measurements and values describe plants grown during the summer in ground beds in an outdoor nursery and in polyethylene-covered greenhouses in Grand Haven, Mich. and under cultural practices typical of commercial production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical Classification

*Buddleia davidii* 'SMNBDL'.

Parentage:

*Female, or seed, parent*.—Proprietary selection of *Buddleia davidii* identified as code designation UC 701, not patented.

*Male, or pollen, parent*.—*Buddleia davidii* 'Pink Delight', not patented.

Propagation:

*Type*.—By softwood stem cuttings.

*Time to initiate roots plant, summer*.—About two to three weeks at temperatures ranging from 21° C. to 29° C.

*Time to produce a rooted plant, summer*.—About 30 days at temperatures ranging from 21° C. to 29° C.

*Root description*.—Medium in thickness, fibrous; typically white in color, actual color of the roots is dependent on substrate composition, water quality, fertilizer, substrate temperature and physiological age of roots.

*Rooting habit*.—Freely branching; dense.

Plant description:

*Plant and growth habit*.—Deciduous perennial shrub; compact, upright and outwardly spreading plant habit; rounded appearance; thick stems, short internodes and dense and bushy appearance; vigorous growth habit.

*Plant height*.—About 60 cm.

*Plant width* (*spread*).—About 83 cm.

*Lateral branches*.—Quantity: Freely branching habit with about eight primary lateral branches developing per plant; pinching enhances lateral branch development. Length: About 48 cm to 52 cm. Diameter: About 8 mm. Internode length: About 4 cm to 4.5 cm. Strength: Strong. Aspect: Erect to about 35° from vertical. Texture: Pubescent; with development, woody. Color, developing: Close to 145C. Color, developed: Close to 199B with striations, close to 199A.

Leaf description:

*Arrangement and appearance*.—Opposite, simple; leaves thick and durable.

*Length*.—About 19.2 cm.

*Width*.—About 6.8 cm.

*Shape*.—Lanceolate.

*Apex*.—Acute to acuminate.

*Base*.—Cuneate.

*Margin*.—Serrate; slightly undulate.

*Texture, upper and lower surfaces*.—Slightly pubescent, coriaceous; venation prominent.

*Venation pattern*.—Pinnate.

*Color*.—Developing leaves, upper surface: Close to 137A; towards the base, close to 138C. Developing leaves, lower surface: Close to 193B. Fully expanded leaves, upper surface: Close to 139A; edges, close to 141A and 141B; venation, close to 145A. Fully expanded leaves, lower surface: Close to 193C; venation, close to 145C.

*Petioles*.—Length: About 5 mm. Diameter: About 2 mm. Texture, upper and lower surfaces: Pubescent. Color, upper and lower surfaces: Close to 145C.

Flower description:

*Flower type and flowering habit*.—Single salverform flowers arranged on terminal and axillary panicles; inflorescences face mostly outwardly; panicles broadly conical in shape; freely flowering habit with more than 1,000 flowers developing per inflorescence; flowers face upright to outwardly depending on position on the panicle; flowers persistent.

*Fragrance*.—Fragrant; sweet, honey-like, pleasant.

*Natural flowering season*.—Long flowering period, plants flower continuously from mid-summer into the early autumn in Michigan.

*Flower buds*.—Height: About 1 cm. Diameter: About 1.5 mm. Shape: Lanceolate. Color: Towards the base, close to 76D; mid-section, close to 81A; towards the apex, close to 83D.

*Inflorescence length*.—About 14 cm to 19.5 cm.

*Inflorescence diameter*.—About 5 cm to 6.5 cm.

*Flower diameter*.—About 7 mm.

*Flower depth*.—About 1.2 cm.

*Petals*.—Quantity per flower: Typically four in a single whorl. Length: About 3 mm. Width: About 3 mm. Shape: Oblong to obovate. Apex: Obtuse. Base: Slightly acute. Margin: Entire; slightly undulate and ruffled. Texture, upper and lower surfaces: Smooth, glabrous; soft. Color: Developing petals, upper and lower surfaces: Close to 86C. Fully developed petals, upper and lower surfaces: Close to 84A; color fades only slightly with development.

*Sepals*.—Quantity per flower: Typically four in a single whorl. Length: About 2 mm. Width: About 0.5 mm. Shape: Narrowly triangular, unguiculate. Apex: Acute. Base: Cuneate. Margin: Entire. Texture, upper and lower surfaces: Slightly pubescent. Color, upper surface: Towards the base, close to 145C and towards the apex, close to 143A. Color, lower surface: Close to 145B.

*Peduncles*.—Length: About 5 mm. Diameter: About 0.5 mm. Strength: Strong. Angle: Upright to outwardly. Texture: Pubescent. Color: Close to 145B.

*Pedicels*.—Length: About 1 mm. Diameter: Less than 1 mm. Strength: Strong. Texture: Smooth, glabrous. Color: Close to 145B.

*Reproductive organs*.—Stamens: Quantity per flower: Typically four. Filament length: About 0.5 mm. Filament color: Close to 26A. Anther length: About 1 mm. Anther shape: Oblong. Anther color: Close to 155B. Pollen amount: Scarce. Pollen color: Close to 11C. Pistils: Quantity per flower: One. Pistil length: About 1 mm. Stigma shape: Oblong. Stigma color: Close to 144B.

*Seeds and fruits*.—Seed and fruit development have not been observed on plants of the new *Buddleia* to date.

Disease & pest resistance: Plants of the new *Buddleia* have not been observed to be resistant to pathogens and pests common to *Buddleia* plants to date.

Garden performance: Plants of the new *Buddleia* have been observed to have good garden performance and tolerate rain, wind and to tolerate temperatures ranging from about −31° C. to about 38° C.

It is claimed:

1. A new and distinct *Buddleia* plant named 'SMNBDL' as illustrated and described.

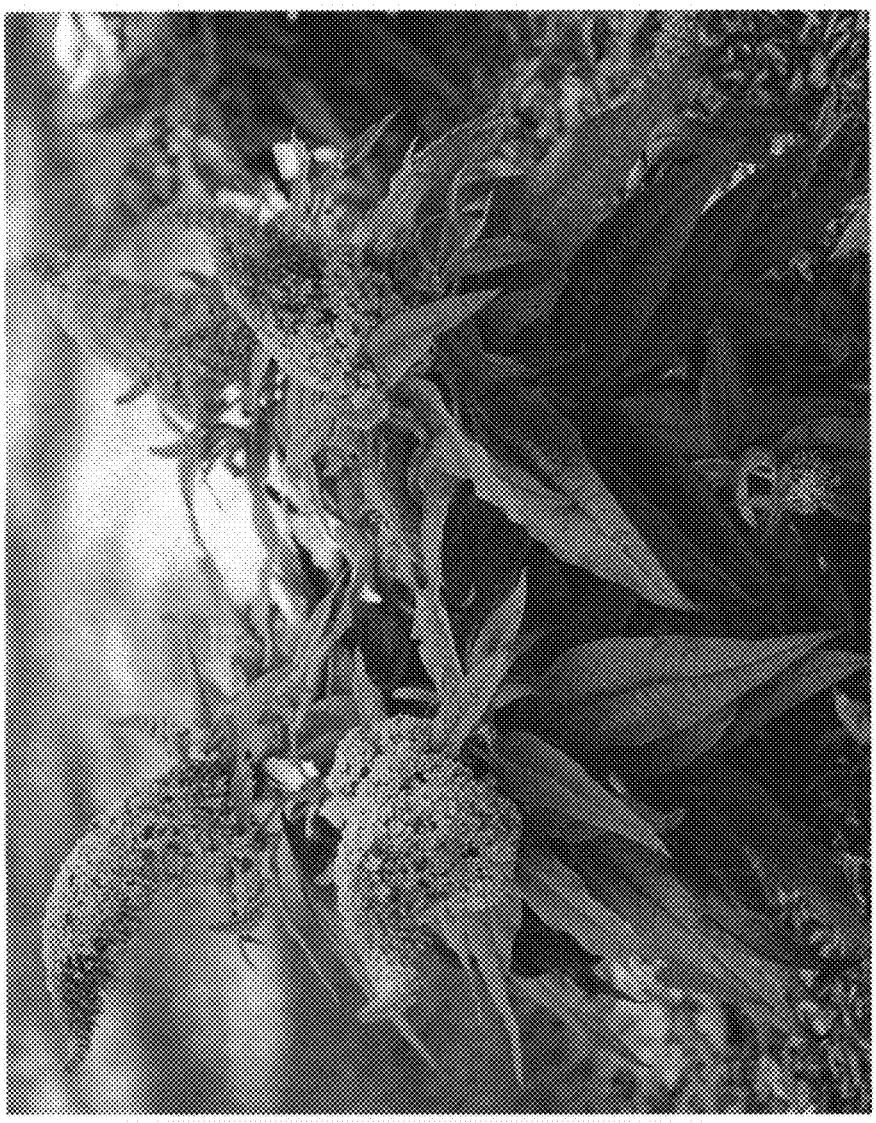

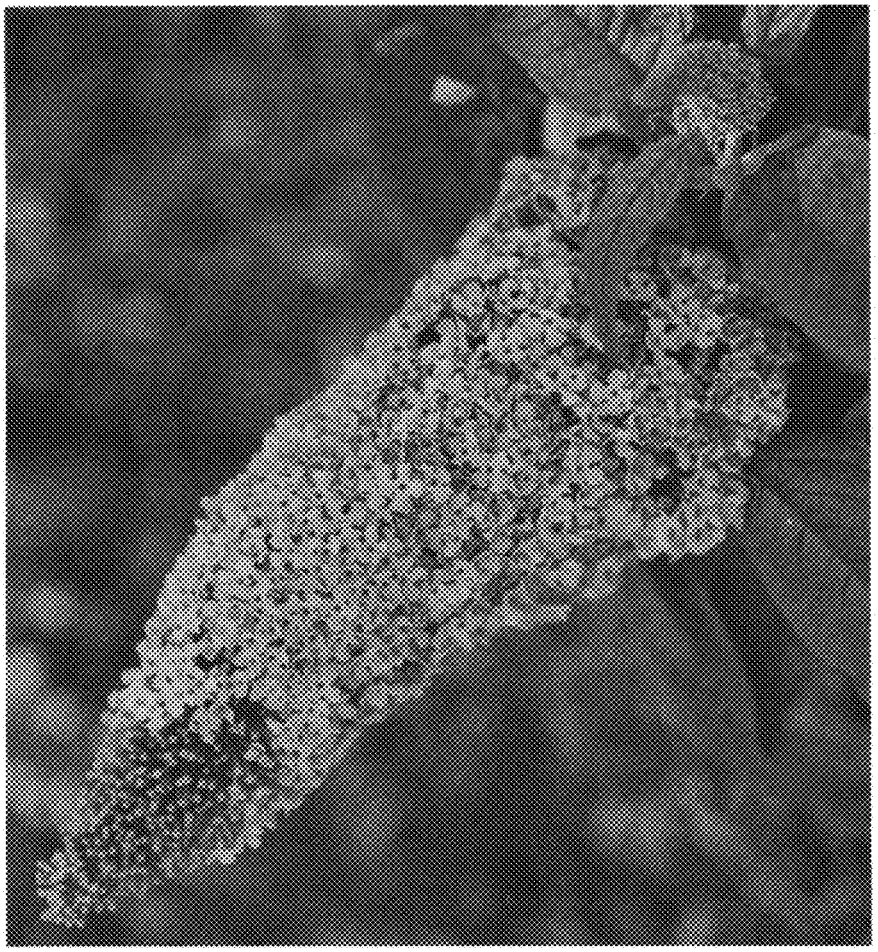

* * * * *